United States Patent
Baricordi et al.

(10) Patent No.: US 10,328,097 B2
(45) Date of Patent: Jun. 25, 2019

(54) GLYCOSAMINOGLYCAN ESTERS, PROCESSES FOR THEIR PREPARATION AND THEIR USE IN FORMULATIONS FOR OPHTHALMIC USE

(71) Applicant: HYALBLUE S.R.L., Lodi (IT)

(72) Inventors: Nikla Baricordi, Occhiobello (IT); Roberto Merighi, Fratta Polesine (IT)

(73) Assignee: Hyalblue S.R.L., Lodi (IT)

( * ) Notice: Subject to any disclaimer, the term of this patent is extended or adjusted under 35 U.S.C. 154(b) by 0 days.

(21) Appl. No.: 15/564,994

(22) PCT Filed: Apr. 7, 2016

(86) PCT No.: PCT/IB2016/051960
§ 371 (c)(1),
(2) Date: Oct. 6, 2017

(87) PCT Pub. No.: WO2016/162809
PCT Pub. Date: Oct. 13, 2016

(65) Prior Publication Data
US 2018/0117077 A1    May 3, 2018

(30) Foreign Application Priority Data
Apr. 7, 2015    (IT) .................. FI2015A0102

(51) Int. Cl.
| A61K 31/727 | (2006.01) |
| A61K 31/726 | (2006.01) |
| A61K 31/728 | (2006.01) |
| A61K 9/00 | (2006.01) |
| C08B 37/00 | (2006.01) |
| C08B 37/08 | (2006.01) |
| A61K 47/61 | (2017.01) |
| C07C 57/03 | (2006.01) |
| C07C 57/13 | (2006.01) |

(52) U.S. Cl.
CPC .......... *A61K 31/727* (2013.01); *A61K 9/0048* (2013.01); *A61K 31/726* (2013.01); *A61K 31/728* (2013.01); *A61K 47/61* (2017.08); *C08B 37/0063* (2013.01); *C08B 37/0069* (2013.01); *C08B 37/0072* (2013.01); *C08B 37/0075* (2013.01); *C07C 57/03* (2013.01); *C07C 57/13* (2013.01)

(58) Field of Classification Search
None
See application file for complete search history.

(56) References Cited

U.S. PATENT DOCUMENTS

| 4,851,521 A * | 7/1989 | della Valle ............. A61K 8/735 536/55.1 |
| 2006/0074048 A1* | 4/2006 | Perbellini ........... C08B 37/0072 514/54 |
| 2014/0094433 A1* | 4/2014 | Liu ........................ A61K 8/738 514/58 |

FOREIGN PATENT DOCUMENTS

| WO | 2004/063364 A1 | 7/2004 |
| WO | WO-2005077176 A1 * | 8/2005 ............. A61K 31/70 |

OTHER PUBLICATIONS

Eroglu, A., & Harrison, E. H. (2013). Carotenoid metabolism in mammals including man: formation, occurrence & function of apocarotenoids. Journal of lipid research, jlr-R039537. (Year: 2013).*
Laabich et al., "Protective Effect of Crocin Against Blue Light- and White Light-Mediated Photoreceptor Cell Death in Bovine and Primate Retinal Primary Cell Culture," Investigative Ophthalmology & Visual Science 47(7):3156-3163 (2006).
Havener et al., "Evaluation of Heparin Therapy of Senile Macular Degeneration," Archives of Ophthalmology 61(3):390-401 (1959).
PCT International Search Report and Written Opinion corresponding to PCT/IB2016/051960, dated Aug. 22, 2016.

* cited by examiner

*Primary Examiner* — Shaojia A Jiang
*Assistant Examiner* — Dale R Miller
(74) *Attorney, Agent, or Firm* — Pepper Hamilton LLP

(57) ABSTRACT

Glycosaminoglycan esters, wherein at least part of the hydroxyl groups present on the N-acetylglucosamine residue are esterified with an apocarotenoid, their preparation, and their use in formulations for ophthalmic use are described.

9 Claims, No Drawings

GLYCOSAMINOGLYCAN ESTERS, PROCESSES FOR THEIR PREPARATION AND THEIR USE IN FORMULATIONS FOR OPHTHALMIC USE

This application is a national stage application under 35 U.S.C. § 371 of PCT Application No. PCT/IB2016/051960, filed Apr. 7, 2016, which claims priority of Italy Application No. FI2015A000102, filed Apr. 7, 2015, which are hereby incorporated by reference in their entirety.

FIELD OF THE INVENTION

The present invention relates to the field of products for ophthalmic use, in particular to esterified glycosaminoglycans useful in protecting eyes from blue light.

BACKGROUND ART

As is known, the electric light has a strong impact on the circadian rhythm; in particular, artificial light hitting the retina between dusk and dawn inhibits the action of neurons which promote sleep, activates the production of orexin in the hypothalamus, and suppresses the nocturnal release of melatonin, which phenomena result in reduction of drowsiness, increased alertness and interference with sleep.

Studies conducted by Czeisler ("Casting light on sleep deficiency" Nature, 497, S13, 2013) show that 30% of American office workers and 44% of night workers complain about sleeping, on average, less than 6 hours a night, while only 3% of the American adult population slept so little in 1960. Moreover, the article notes that optoelectronic devices with light emitting diodes (LED), such as television, computer screens, laptops, tablets and mobile phones, use a type of white light which is rich in blue light. The ipRGCs (photosensitive ganglion cells), which are found in the eye, are more sensitive to light which is visible at low wavelengths (blue and green), says Czeisler, therefore the exposure to LEDs in night hours generally causes a greater interruption of circadian rhythm, melatonin secretion and sleep compared to night exposure to light from light bulbs.

Further studies, conducted by Masuda and Watanabe (Short Wavelength Light-Induced Retinal Damage in Rats. Jpn J. Ophthalmol., 44:615-61 9, 2000) showed that the light at wavelengths of 350 nm causes damage to photoreceptor cells, while light at wavelengths of 441 nm damages the retinal pigment epithelium. In an article entitled "Evaluation of Blue-Light Hazards from Various Light Sources", 2002, Progress in lens and Cataract Research, Tsutomu Okuno stresses that an average exposure of 270 seconds a day to the blue light of the LEDs can lead to photochemical retinal damage.

This type of damage to the retina has been studied by Elawady A. Ibrahim (Neuroprotective Effects of Grape Seeds against Photo-Chemical Damage-Induced Retinal Cell Death. Nature and Science 9(11):83-89, 2011): he argues that prolonged exposure to blue light permanently damages the retinal neurons.

Roehlecke et al. (Influence of blue light on photoreceptors in a live retinal explants system. Molecular Vision 17: 876-884, 2011) also reported in vitro studies in which the irradiation of blue light on retinal transplants produces ultra-structural changes involving necrosis of the photoreceptor cells.

Recently, in vitro and in vivo studies have shown that the irradiation of blue light at 470 nm affects the central nervous system, can cause the complete reset of the circadian rhythm (Jones—Manipulating circadian clock neuron firing rate resets molecular circadian rhythms and behavior—Nature Neuroscience, Advance Online Publication).

Although physical protections against blue light (such as spectacles and screens for monitors) are available on the market, these solutions are usually bulky or expensive.

In addition, although contact lenses are available for this purpose, the latter involve the same side effects (e.g. hyperemia, eye infections, corneal ulcers) as conventional lenses.

It is also known that carotenoids are a class of organic compounds present in plants and other photosynthetic organisms. They are usually divided into two classes, depending on the presence or absence of oxygen atoms within the molecule: the first is that of xanthophylls, while the last comprises carotenes. The color of these molecules ranges from light yellow to bright red depending on the type of wavelengths absorbed and reflected.

It has been widely documented that a diet based on carotenoids protects from damage caused by free radicals since these compounds, rich in double PI bonds, can oxidize and eliminate noxious species from the body.

The oxidative degradation products, called apocarotenoids, are in many cases molecules with further beneficial effects, as in the case of vitamin A (retinol, retinoic acid, retinal), bixin and crocetin.

Apocarotenoids are able to absorb blue light, as in the case of bixin (Food Chemistry 141; 4: 3906-3912, 2013) and crocin, the ester of crocetin (Invest. Ophthalmol. Vis. Sci. 47: 3156-3163, 2006).

To date, there are no chemical compounds on the market capable of ensuring an effective protection of eyes from blue light; WO 2004/063363 describes hyaluronic acid retinoic esters as useful products for the differentiation of totipotent stem cells. On the other hand, it is also known that eye drops are not optimal methods for the administration of active ingredients, since they have low bioavailability and are thus subject to a low therapeutic response, mainly due to the presence, in the eye, of drainage systems: for this reason, products of this type require multiple applications in order to achieve the desired therapeutic effect.

The interest in developing compounds which are able to protect the eyes from damage caused by blue light radiation is apparent from the above.

DETAILED DESCRIPTION OF THE INVENTION

The present invention allows to overcome the aforesaid drawbacks with new glycosaminoglycan esters, wherein at least part of the hydroxyl groups present on the N-acetylglucosamine residue are esterified with an apocarotenoid.

Glycosaminoglycan according to the invention refers to, for example: hyaluronic acid, chondroitin sulfate, heparin, heparan sulfate; hyaluronic acid is preferred.

Among the apocarotenoids usable according to the invention we may mention: retinoic acid, crocetin, bixin, abscisic acid.

Hyaluronic acid (hereinafter, HA) is a natural linear polysaccharide consisting of alternating residues of D-glucuronic acid and N-acetyl-D-glucosamine into repeating units.

HA may be used in pure form as a drug for disorders arising from dry eye syndrome, such as keratoconjunctivitis sicca, as described by DeLuise (Annals of Ophthalmology 16: 823-824, 1984), Laflamme (Canadian Journal of Ophthalmology 23: 174-176, 1988) and Sand (Acta Ophthalmologica 67: 181-183, 1989).

It is noted that according to the present invention, in contrast to the occurrence in other eye drops, hyaluronic acid is not used as an excipient but forms a new chemical product by reacting with the apocarotenoid.

The products according to the present invention can be prepared according to processes known in art; in particular following the process described in US 20090239822.

For example, a hyaluronic acid tetrabutylammonium (HA-TBA) salt is first prepared by salifying an ionic exchange resin (such as Amberlite®) with an aqueous solution of tetrabutylammonium hydroxide (TBAI) which is percolated on the resin arranged in a chromatographic column.

Once all the solution has passed, the resin is washed with water and then a solution of sodium hyaluronate dissolved in water is passed on the salified resin and finally the eluate is collected and freeze-dried.

Normally, the aqueous tetrabutylammonium hydroxide solution has a concentration of 15-45%, preferably 30-40%, more preferably 40%; while the sodium hyaluronate solution in water normally has a concentration of 1.5-4.5 g/L, preferably 3 g/L.

The salt (HA-TBA) obtained as described above is then reacted with the selected apocarotenoid under heating. The carboxyl function of the apocarotenoid is activated by reaction with carbonyldiimidazole at room temperature; the resulting compound is added slowly to the HA-TBA gel in dimethylformamide.

The mixture is left under stirring between 25 and 35° C. for 12-20 h, then the product is precipitated by the addition of sodium chloride and ethanol.

The degree of substitution of apocarotenoid in the esters according to the invention is of 0.1-5%, where the term "degree of substitution" indicates the number of moles of apocarotenoid per mole of glycosaminoglycan.

The esters according to the invention normally have a molecular weight of 350,000-2,000,000 Daltons, thus indicating the average molecular weight of the glycosaminoglycan without considering the contribution of the apocarotenoid residue.

The compounds according to the present invention can be formulated in the forms known in pharmacopeia as suitable for ocular administration.

For example, they can be formulated as a 0.1-1% solution of compound in purified water, with the possible addition of polyethylene glycols to increase viscosity and benzalkonium chloride or chlorhexidine as preservatives (alternatively, single-dose packaging may be considered).

The examples below illustrate what is claimed in higher detail.

Example 1

Preparation of the Hyaluronic Acid Tetrabutylammonium (HA-TBA) Salt

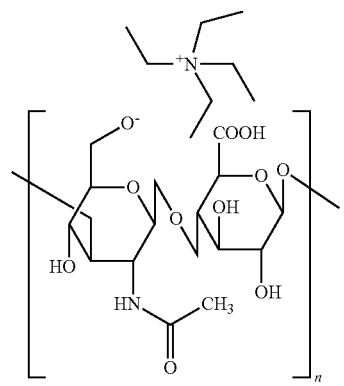

where n is between 250 and 5000.

An ion-exchange resin (Amberlite® in acid form) is used, having a capacity of 1.9 eq/L.

1 L of resin is loaded into a chromatographic column and is then washed with demineralized water and then an aqueous solution of 40% tetrabutylammonium hydroxide (TBAI) is percolated on the resin from above by means of a peristaltic pump.

Once all the solution has passed, the resin is washed with demineralized water until the eluate has a constant pH of 9.5-10.

One liter of resin thus salified allows to salify about 75-80 g of sodium hyaluronate. The sodium hyaluronate is dissolved in water (concentration of about 3 g/L) and the resulting gel is passed in a column containing the previously prepared resin. The eluate is collected and freeze-dried.

Example 2

Preparation of a Hyaluronic Acid Ester with Crocetin

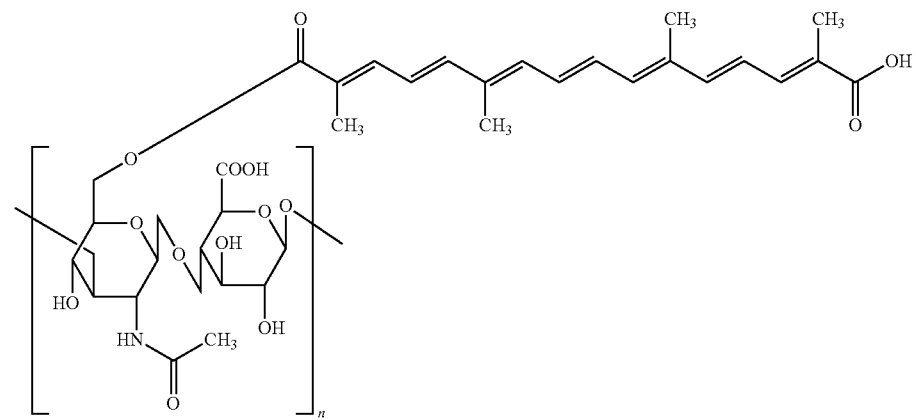

where n is between 250 and 5000

1.5 g HA-TBA is dissolved in 500 mL DMF in a reactor with thermostat and is placed under stirring at 30° C.

0.8 g crocetin is dissolved in 400 mL DMF in a reactor protected against moisture and 1 eq N,N-carbonyldiimidazole is added to the mixture.

After 1 h, the solution is slowly added to the HA-TBA gel and the mixture thus obtained is allowed to stir at 30° C. for 16 h.

The reaction is stopped by the addition of 90 mL of saturated solution of sodium chloride. The product is precipitated by the addition of a 96% volume of ethanol; the supernatant is discarded and the filtered residue is washed several times with ethanol in different concentrations and then dried under vacuum.

The resulting product has a degree of substitution of 0.5%.

Example 3

Preparation of a Hyaluronic Acid Ester with Crocetin 1.5 g HA-TBA is dissolved in 500 mL DMF in a reactor with thermostat and is placed under stirring at 30° C.

0.4 g crocetin is dissolved in 200 mL DMF in a reactor protected against moisture and 1 eq N,N-carbonyldiimidazole is added to the mixture.

After 1 h, the solution is slowly added to the HA-TBA gel and the mixture thus obtained is allowed to stir at 30° C. for 16 h.

The reaction is stopped by the addition of 70 mL of saturated solution of sodium chloride. The product is precipitated by the addition of a 96% volume of ethanol; the supernatant is discarded and the filtered residue is washed several times with ethanol in different concentrations and then dried under vacuum.

The resulting product has a degree of substitution of 0.25%.

Example 4

Preparation of a Hyaluronic Acid Ester with Bixin 1.5 g HA-TBA is dissolved in 500 mL DMF in a reactor with thermostat and is placed under stirring at 30° C.

0.95 g bixin is dissolved in 450 mL DMF in a reactor protected against moisture and 1 eq N, N-carbonyldiimidazole is added to the mixture.

After 1 h, the solution is slowly added to the HA-TBA gel and the mixture thus obtained is allowed to stir at 30° C. for 16 h.

The reaction is stopped by the addition of 90 mL of saturated solution of sodium chloride. The product is precipitated by the addition of a 96% volume of ethanol; the supernatant is discarded and the filtered residue is washed several times with ethanol in different concentrations and then dried under vacuum.

The resulting product has a degree of substitution of 0.4%.

Example 5

Preparation of a Hyaluronic Acid Ester with Bixin 1.5 g HA-TBA is dissolved in 500 mL DMF in a reactor with thermostat and is placed under stirring at 30° C.

0.5 g bixin is dissolved in 250 mL DMF in a reactor protected against moisture and 1 eq N, N-carbonyldiimidazole is added to the mixture.

After 1 h, the solution is slowly added to the HA-TBA gel and the mixture thus obtained is allowed to stir at 30° C. for 16 h.

The reaction is stopped by the addition of 80 mL of saturated solution of sodium chloride. The product is precipitated by the addition of a 96% volume of ethanol; the supernatant is discarded and the filtered residue is washed several times with ethanol in different concentrations and then dried under vacuum.

The resulting product has a degree of substitution of 0.15%.

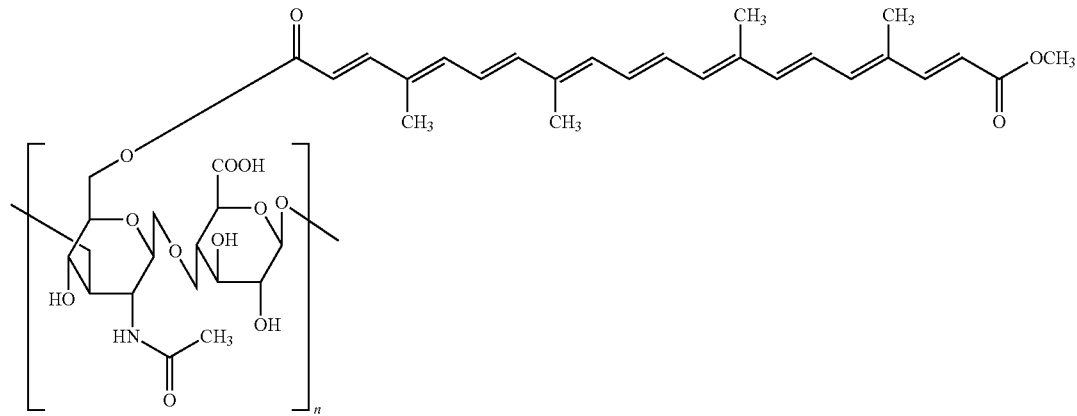

where n is between 250 and 5000

Example 6

Preparation of a Hyaluronic Acid Ester with Retinoic Acid

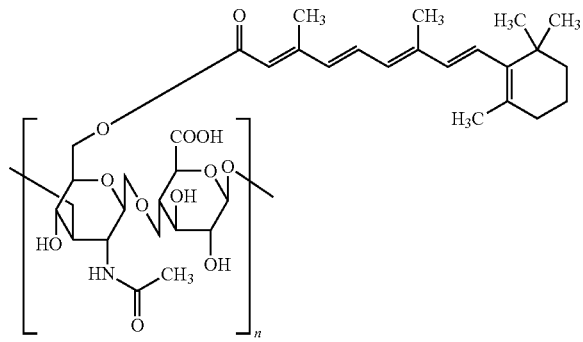

where n is between 250 and 5000.

1.5 g HA-TBA is dissolved in 500 mL DMF in a reactor with thermostat and is placed under stirring at 30° C.

0.7 g retinoic acid is dissolved in 350 mL DMF in a reactor protected against moisture and 1 eq N,N-carbonyldiimidazole is added to the mixture.

After 1 h, the solution is slowly added to the HA-TBA gel and the mixture thus obtained is allowed to stir at 30° C. for 16 h.

The reaction is stopped by the addition of 90 mL of saturated solution of sodium chloride. The product is precipitated by the addition of a 96% volume of ethanol; the supernatant is discarded and the filtered residue is washed several times with ethanol in different concentrations and then dried under vacuum.

The resulting product has a degree of substitution of 0.2%.

The invention claimed is:

1. Glycosaminoglycan ester, wherein at least some hydroxyl groups present on N-acetylglucosamine residues of the glycosaminoglycan ester are esterified with an apocarotenoid, wherein said apocarotenoid is selected from crocetin, bixin, or abscisic acid.

2. Ester according to claim 1, wherein said glycosaminoglycan ester comprises glycosaminoglycans selected from: hyaluronic acid, chondroitin sulfate, heparin, or heparan sulfate.

3. Ester according to claim 1, wherein the degree of esterification of apocarotenoid in the ester is from 0.1 to 5% and the molecular weight of said ester is from 350,000 to 2,000,000 Daltons.

4. A process for preparing ester according to claim 1, wherein said method comprises:
    preparing a hyaluronic acid tetrabutylammonium salt by salifying an ionic exchange resin with an aqueous solution of tetrabutylammonium hydroxide;
    washing the resin with water and passing a solution of sodium hyaluronate dissolved in water therethrough, thus collecting the eluate containing said salt and freeze-drying it;
    reacting the thus-obtained salt under heating with a selected apocarotenoid to form a reaction mixture, wherein carboxy functionality of said apocarotenoid is activated by reaction at room temperature with carbonyldiimidazole in dimethylformamide;
    stirring the reaction mixture; and
    precipitating the ester product by addition of sodium chloride and ethanol.

5. A method for protecting eyes of an individual from blue light comprising: administering to the eyes of the individual an effective amount of a glycosaminoglycan ester, wherein at least some hydroxyl groups present on N-acetylglucosamine residues of the glycosaminoglycan ester are esterified with an apocarotenoid, wherein said apocarotenoid is selected from crocetin, bixin, or abscisic acid.

6. The method according to claim 5, wherein said glycosaminoglycan ester comprises glycosaminoglycans selected from: hyaluronic acid, chondroitin sulfate, heparin, or heparan sulfate.

7. A formulation for ophthalmic use, comprising at least one glycosaminoglycan ester according to claim 1.

8. A formulation according to claim 7, wherein said formulation comprises a 0.1-1% glycosaminoglycan ester solution in purified water.

9. The formulation of claim 8, further comprising one or more of polyethylene glycols, benzalkonium chloride, or chlorhexidine.

* * * * *